United States Patent
Marcos Rodríguez et al.

(10) Patent No.: US 7,799,540 B2
(45) Date of Patent: Sep. 21, 2010

(54) **METHOD OF PRODUCING LYCOPENE THROUGH THE FERMENTATION OF SELECTED STRAINS OF *BLACKESLEA TRISPORA*, FORMULATIONS AND USES OF THE LYCOPENE THUS OBTAINED**

(75) Inventors: Ana Teresa Marcos Rodríguez, León (ES); Antonio Estrella De Castro, León (ES); Javier Costa Perez, León (ES); Manuel Antonio Oliver Ruiz, León (ES); Nieves Fraile Yecora, León (ES); Juan Luis De La Fuente Moreno, León (ES); Marta Rodríguez Saiz, León (ES); Bruno Diez Garcia, León (ES); Enrieque Peiro Cezon, León (ES); Angel Muñoz Ruiz, León (ES); Walter Cabri, León (ES); Juan Francisco Lopez Ortiz, León (ES); José Luis Barredo Fuente, León (ES)

(73) Assignee: Vitatene, S.A., Leon (ES)

( * ) Notice: Subject to any disclaimer, the term of this patent is extended or adjusted under 35 U.S.C. 154(b) by 271 days.

(21) Appl. No.: 10/498,682

(22) PCT Filed: Dec. 20, 2002

(86) PCT No.: PCT/ES02/00610

§ 371 (c)(1),
(2), (4) Date: Dec. 17, 2004

(87) PCT Pub. No.: WO03/056028

PCT Pub. Date: Jul. 10, 2003

(65) Prior Publication Data

US 2005/0106657 A1  May 19, 2005

(30) Foreign Application Priority Data

Dec. 31, 2001 (ES) ............................... 200102925

(51) Int. Cl.
*C12P 23/00* (2006.01)
*C12P 5/00* (2006.01)
*C07C 403/00* (2006.01)

(52) U.S. Cl. .................. 435/67; 435/166; 435/167; 585/16; 585/351; 585/809

(58) Field of Classification Search ............... 585/351; 435/166, 67
See application file for complete search history.

(56) References Cited

U.S. PATENT DOCUMENTS

| 5,208,381 | A * | 5/1993 | Meyer | 568/10 |
| 5,858,700 | A * | 1/1999 | Ausich et al. | 435/67 |
| 6,235,315 | B1 * | 5/2001 | Runge et al. | 424/489 |
| 2006/0105443 | A1 * | 5/2006 | Wu et al. | 435/170 |

FOREIGN PATENT DOCUMENTS

| ES | 2 156 735 | | 7/2001 |
| ES | 2 157 166 | | 8/2001 |
| FR | 1 403 839 | | 6/1965 |
| WO | WO 01/12832 | * | 2/2001 |

OTHER PUBLICATIONS

Heinonen et al "Carotenoids in Finnish Foods: Begetables, Fruits, and Berries" 1989 vol. 37 pp. 655-659.*

* cited by examiner

*Primary Examiner*—Herbert J. Lilling
(74) *Attorney, Agent, or Firm*—Ladas and Parry LLP (57) ABSTRACT

The method of fermentation with selected strains of *B. trispora* described in the present invention makes it possible to achieve lycopene yields higher than those currently described. The methods of isolation, purification and formulation are applicable to any natural source of lycopene, especially to submerged cultures of mucoral fungi of the genera *Blakeslea, Choanephora, Phycomyces* or *Mucor*. The method of extraction makes it possible to simplify the recovery process and increase the purity of the product, relative to the methods previously described. The methods of formulation provide high added value, since they make it possible to obtain stabilized preparations of lycopene for direct application in the food and pharmaceutical fields.

51 Claims, 2 Drawing Sheets

METHOD OF PRODUCING LYCOPENE THROUGH THE FERMENTATION OF SELECTED STRAINS OF *BLACKESLEA TRISPORA*, FORMULATIONS AND USES OF THE LYCOPENE THUS OBTAINED

FIELD OF THE INVENTION

The method of fermentation with selected strains of *B. trispora* described in the present invention makes it possible to achieve levels of production of lycopene higher than those currently described. The methods of isolation, purification and formulation are applicable to any natural source of lycopene, and especially to submerged cultures of mucoral fungi of the genera *Blakeslea, Choanephora, Phycomyces* or *Mucor*. The method of extraction provides a simplification of the recovery process and an increase in product purity relative to the methods previously described. The methods of formulation give high added value, as they make it possible to obtain stabilized preparations of lycopene for direct application in the foodstuffs and pharmaceutical fields.

STATE OF THE ART

The carotenoids are widely distributed in nature, imparting their characteristic color, from yellow to dark red, to numerous natural substances such as carrots, peppers, tomatoes, flowers or certain microorganisms, including some bacteria, fungi and photosynthetic organisms. The carotenoids can be divided into two types: (i) pure hydrocarbons called carotenes, including compounds such as β-carotene, α-carotene, γ-carotene or lycopene and (ii) molecules called xanthophylls, which contain oxygen in various forms (hydroxyl groups, epoxy groups, etc.), including astaxanthin, zeaxanthin, capsanthin, cantaxanthin, lutein, etc. The two groups of compounds display different behavior with respect to their physicochemical properties and solubility in organic solvents. All these compounds play an important role in the human diet, their properties having been studied extensively as antioxidants for the prevention of cancer and other human diseases and as precursors of vitamin A. It has recently been demonstrated in rats that lycopene inhibits the harmful effect of ferric nitriloacetate on DNA and prevents necrosis of the liver [Matos H.R. et al. (2001) Arch. Biochem. Biophys. Vol. 396]. In addition, owing to their colorations from yellow to red, the carotenoids are of considerable commercial importance as colorants and food additives on account of their beneficial effects on health and their attractive colors [Ninet L. and Renaut J. (1979) In: Peppler H J., Perlman D. (eds). Microbial Technology, 2nd Edition, Vol. 1, Academic Press, New York, pp. 529-544].

Lycopene ($C_{40}H_{56}$) is an intermediate in the biosynthetic pathway of β-carotene and the xanthophylls. It has a molecular weight of 536.85 and the following molecular formula:

Lycopene

As well as acting as an antioxidant, lycopene prevents cardiovascular diseases and some types of cancer and is active in growth control [Giovannucci et al. (1995) J. Nat. Cancer Inst. 87: 1767-1776; Stahl W. and Sies, H. (1996) Arch. Biochem. Biophys. 336: 1-9; Clinton, S K. (1998) Nutr. Rev. 56: 35-51]. This has led to increased demand on the part of consumers. Production of lycopene as a high-purity compound has been linked in the past to chemical synthesis [U.S. Pat. Nos. 5,208,381; 5,166,445; 4,105,855; 2,842,599]. However, alternative routes now exist, based on sources of lycopene of natural origin and special extraction processes.

The production of carotenoids by microbial biosynthesis is a classic example of competition between chemical and biological processes. Lycopene preparations of biological origin are obtained from tomato [PCT WO 97/48287, EP 608027] or by fermentation of mucoral fungi of the genera *Phycomyces, Blakeslea* and *Choanephora* [GB 1008469, U.S. Pat. Nos. 3,097,146, 3,369,974, JP 73016189, JP 73016190, RU 2102416, WO 00/77234]. To achieve a maximum yield of carotenoids with *B. trispora* it is necessary to ferment the (+) and (−) strains together [Ciegler, A. (1965) Advances in Applied Microbiology 7: 1-34; Plempel, M. (1965) Planta 65:225-231; Sutter, R P. and Rafelson, M E. (1968) J. Bacteriology 95: 426-432]. The increase in yield of carotenoids in mixed cultures is related to the production of a family of acid compounds called factor β or trisporic acids [WO 00/77234, Caglioti L. et al. (1966) Tetrahedron Supplement 7: 175-187]. For the biosynthesis of trisporic acids, the β-carotene produced by the (+) and (−) strains is metabolized by both to retinal and subsequently to 4-dihydrotrisporol. The (+) strain utilizes the 4-dihydrotrisporol as substrate for forming dihydrotrisporic acid and its methyl ester (methyl-4-dihydrotrisporate). For its part, the (−) strain metabolizes the 4-dihydrotrisporol to trisporol. Finally, the methyl-4-dihydrotrisporate is converted to trisporic acid by the (−) strain and the trisporol is converted to trisporic acid by the (+) strain. This description of the biosynthesis of the trisporic acids is a simplification, since during the process many co-metabolites are generated, some of which are common to both strains (+) and (−), but others are specific to one of them. The relative quantities of these co-metabolites vary depending on the strains.

The biosynthetic pathway of β-carotene (see scheme 1) has been described in fungi that are related phylogenetically to *B. trispora* such as *Phycomyces blakesleeanus* and *Mucor circinelloides* [Arrach N. et al. (2001) Proceedings of the National Academy of Sciences USA 98: 1687-1692; Velayos A. et al. (2000) European Journal of Biochemistry 267: 5509-5519]. At least three enzymes are necessary for said biosynthesis: (i) phytoene synthase, which joins together two molecules of geranylgeranyl pyrophosphate to form phytoene, (ii) phytoene dehydrogenase, which introduces four double bonds into the phytoene molecule to synthesize lycopene, and (iii) lycopene cyclase, which, using lycopene as substrate, forms the rings located at the two ends of the β-carotene molecule. It was concluded on the basis of analysis of mutants of *B. trispora* that the biosynthetic pathway of β-carotene in this fungus is similar to that described for *P. blakesleeanus* [Metha B. J. and Cerdá-Olmedo E. (1995) Applied Microbiology and Biotechnology 42: 836-838]. In the case of *P. blakesleeanus*, the yellow color of its mycelium can be altered by mutation, giving rise to strains with mycelium colored red, white or various shades of yellow. The red mutants accumulate lycopene, whereas the white ones lack production of carotenoids or accumulate phytoene. For production of lycopene it is necessary to have strains of *B. trispora* that lack lycopene cyclase activity, or alternatively chemicals that inhibit said enzymatic activity must be added to the fermentation medium.

SCHEME 1

Patents GB 1008469, U.S. Pat. Nos. 3,097,146, 3,369,974, JP 73016189, JP 73016190, RU 2102416 and WO 00/77234 describe the production of lycopene by means of fermentation of mucoral fungi such as *Phycomyces, Blakeslea* and *Choanephora*. Patents GB 1008469 and U.S. Pat. No. 3,097,146 describe methods of fermentation of *B. trispora* based on control of the pH between values of 7.0 and 9.5, obtaining yields of 99.7 mg/l of lycopene after 7 days of fermentation. Patents JP 73016189 and JP 73016190 describe methods of production of lycopene with mucoral fungi based on the addition of tertiary amines. Patent RU 2102416 describes the addition of aminomethylpyridines and tobacco residues for inducing the accumulation of lycopene. As well as the substances described in said patents, the use of other nitrogenated heterocyclic bases for blocking the synthesis of carotenoids at the lycopene level has been published: nicotine [JP 09313167], imidazole, pyridine, morpholine, quinoline and some substituted derivatives [U.S. Pat. No. 3,369,974; Ninet L., Renaut J. (1979) In: Peppler H J, Perlman D (eds). Microbial Technology, 2nd Edition, Vol. 1, Academic Press, New York, pp. 529-544]. Moreover, mutants of *B. trispora* that accumulate lycopene without the need to add tertiary amines have been described [Mehta B. J. and Cerdá-Olmedo E. (1995) Appl. Microbiol. Biotechnol. 42: 836-838].

In addition to the aforementioned mucoral fungi, production of lycopene has been described with algae [JP 09313167 and JP 2000152778], by fermentation of *Streptomyces chrestomyceticus* var. rubescens [U.S. Pat. No. 3,467,579] and by modifying the biosynthetic pathway of carotenoids of *Flavobacterium* sp. R1534 [U.S. Pat. No. 6,124,113].

Lycopene can be obtained from plant products such as: tomato, carrot, peppers, vegetable oils, etc. Thus, patent WO 97/48287 describes a method for the preparation of lycopene-rich oleoresins from tomatoes by pressing the tomatoes until the pulp is obtained, extraction of lycopene from the pulp with organic solvents and subsequent elimination of the solvent by evaporation, giving rise to an oleoresin with a lycopene content in the range 2-10%. Similar methods of obtaining oleoresins rich in carotenoids in general and lycopene in particular from plants and oils are described in various patents, such as in U.S. Pat. No. 5,245,095 and EP 580745, by precipitation with calcium salts, in U.S. Pat. No. 5,019,668, using a method of transesterification with oils followed by distillation, in WO 95/16363, which describes the fractionation of the tomato into various fractions that include an oleoresin rich in carotenoids, and in PCT WO 90/08584, which describes the extraction of lycopene by using fluids in a supercritical state, although the extract obtained is a mixture of various carotenoids and the extraction yields are very low owing to their low solubility.

In all these cases, owing to the low concentration of lycopene in these natural products and the intracellular location of this compound in certain organelles such as chloroplasts or chromoplasts, the extraction yields and the purity of the product obtained are low, obtaining oleoresins rich in lycopene or dehydrated raw products together with varying amounts of other carotenoid or non-carotenoid compounds. In the majority of cases the methods of extraction described require preparation of the fruit by milling or pressing to facilitate extraction of the solvent and thus release the lycopene-rich intracellular contents. Finally, most of the processes described in these patents require the use of organic solvents that are present as traces in the oleoresin obtained. Furthermore, patent IL 107999 describes the preparation of oleoresins that are very rich in lycopene from tomato pulp, although, as previously, the product obtained does not consist of lycopene crystals of high purity, but of lycopene-rich lipid concentrates.

On the other hand, patent WO 97/15554 describes the extraction of carotenoids of plant origin from carrots and tomatoes, which include lycopene, by isolation of chloroplasts and chromoplasts, followed by digestion of said organelles with hydrolytic enzymes of proteins such as pectins and/or proteases that make it possible to release the lycopene bound to various structural proteins. By subsequent alkaline treatment and extraction with alcoholic mixtures of low molecular weight it is possible to obtain lycopene extracts with a richness and purity greater than the oleoresins, though without obtaining purified crystals of lycopene but lycopene-rich raw extracts. Similarly, concentrated extracts of lycopene are obtained in patent EP 608027 A2 by isolation of tomato chromoplasts in which lycopene occurs in crystalline form. These extracts from lycopene-rich tomato chromoplasts are used directly as colorants without subsequent extraction of the lycopene crystals, avoiding the color change of the lycopene during extraction and making the use of organic solvents unnecessary. In accordance with the method described in this patent, it is not possible to obtain pure lycopene in crystalline form suitable for use in foodstuff or pharmaceutical compositions, but only as food colorant in dehydrated, freeze-dried or frozen form.

Certain carotenoid-rich micro-algae of the *Dunaliella* type are another important source of lycopene. There are various methods of extracting carotenoids, and lycopene in particular, from these organisms, as is reflected in patents U.S. Pat. Nos. 5,378,369, 4,713,398 and 4,680,314, by extraction with organic solvents (chlorocarbons, hydrocarbons, etc.) or edible oils (DE 4342798). A different process is described in PCT WO 98/08584, where a lycopene extract is obtained using $CO_2$ in a supercritical state, although the extract thus obtained is of low purity with respect to lycopene.

Lycopene can also be obtained from certain mucoral fungi such as *Blakeslea, Choanephora, Phycomyces* or *Mucor* by fermentation in a liquid medium, offering as an advantage over the production of lycopene from plant products or algae the increased concentration of this compound, in some cases above 5 wt. % relative to the quantity of dry biomass, concentrations that are higher than those obtained from the best plant varieties, as well as the possibility of the biotechnological development of overproducing strains of these microorganisms, either by techniques of classical mutagenesis or by the application of new technologies of molecular biology that permit the genetic manipulation of these microorganisms, increasing the concentration and yield of lycopene, and eliminating the production of other structurally related carotenoids.

As already mentioned, the preparation of crystalline lycopene of high purity from natural sources generally requires a stage of extraction with organic solvents or fluids in a supercritical state and then various additional purification stages such as chromatography, processes of adsorption and elution and stages of precipitation or crystallization, as described for example in patents U.S. Pat. No. 3,369,974, EP 818255 and EP 242148. In the majority of cases in which these stages of subsequent purification are not used and crystallization is carried out directly from the extract by evaporation of the solvent until the solubility is overcome, the purity of the product obtained is very low and it is subsequently necessary to carry out processes of recrystallization of the lycopene obtained, with the added difficulty that the low solubility of the product means a large quantity of solvent must be used to achieve the stage of recrystallization, which leads in addition to a low yield (NL 6411184, U.S. Pat. No. 4,439,629).

Patent application WO 96/13178 describes the preparation of concentrates of stabilized crystalline lycopene in a foodstuffs-compatible liquid medium in which lycopene is insoluble, such as ethylene glycol, ethanol or glycerol, obtaining, by milling, small crystals (1-3 microns) of lycopene suspended in a liquid medium. Moreover, patent application WO 98/43620 describes a method of isolating lycopene crystals from an oleoresin by saponification of various triglycerides and phosphonates at high temperature and then dilution with water, obtaining lycopene crystals of purity between 75% and 95%. A similar method was recently described for the preparation of crystals of β-carotene of high purity in PCT WO 98/03480 by washing with water, alcohols of low molecular weight or acetone, though its application for obtaining lycopene crystals of high purity has not been described.

The instability of the carotenoids in crystalline form is well known, and one method of stabilizing them is the preparation of oily dispersions. Moreover, it is believed that carotenoids dispersed in oil are absorbed more easily by the body. An alternative method for the stabilization of unstable compounds is their microencapsulation in starch matrices. Thus, patents U.S. Pat. Nos. 2,876,160, 2,827,452, 4,276,312 and 5,976,575 describe a considerable increase in the stability of various compounds, including the carotenoids, by encapsulating them in a starch matrix.

One of the main difficulties in using carotenoids in the field of colorants is their zero solubility in water, since many of their applications take place in aqueous media. This problem of solubility was mentioned in document U.S. Pat. No. 3,998,753, and was solved by preparing solutions of carotenoids in volatile organic solvents, such as halogenated hydrocarbons, and emulsifying them with an aqueous solution of sodium lauryl sulfate.

U.S. Pat. No. 5,364,563 describes a method of producing a preparation of carotenoids in powder form, which involves forming a suspension of a carotenoid in oil with a high boiling point. The suspension is superheated with steam for a maximum period of 30 seconds in order to form a solution of carotenoid in oil. Next, this solution is emulsified over an aqueous solution of a colloid and then the emulsion is spray-dried.

DETAILED DESCRIPTION OF THE DIAGRAMS

DETAILED DESCRIPTION OF THE INVENTION

The present invention describes a series of methods for obtaining high yields of lycopene with the fungus *B. trispora*, as well as methods for its recovery and formulation. The invention consists of (i) the design of methods for obtaining and selecting mutants of *B. trispora* that are overproducers of lycopene, (ii) the development of improved conditions of fermentation, (iii) the establishment of processes for recovering lycopene from the mycelium and (iv) the achievement of formulations that overcome the problems of stability and solubility in various media, present in the state of the art. *B. trispora* is a fungus that is of great industrial importance for the biotechnological production of lycopene. In fact, said process proves to be competitive with the synthetic process used industrially at present.

With the aim of obtaining strains that are overproducers of lycopene, in the first place a mutagenic method was developed for the (+) and (−) strains of *B. trispora* with the mutagenic agents ethylmethane sulfonate (EMS) and N-methyl-N'-nitro-N-nitrosoguanidine (NTG). The suspensions of spores for mutation were obtained from slants with YpSs medium. The spores were resuspended by adding 10 ml of a solution of Triton X-100 at 0.1% to each slant. The mycelium residues were removed by filtration through a nylon filter with a pore size of 20 μm. The concentration of spores in the suspension was adjusted to $10^6$ spores/ml. The method of mutation with EMS consisted of incubating $10^6$ spores/ml in a 3% EMS solution in 0.1 M sodium phosphate buffer pH 7.0 at room temperature for 60 minutes, achieving mortality rates of around 99%. The mutated spores were washed three times with 0.1% Triton X-100 and centrifuged at 3000 rpm at 15° C. for 2 minutes. The method of mutation with NTG consisted of incubating 106 spores/ml in a solution that contained 250 μg/ml of NTG and 0.1 M sodium citrate buffer pH 5.0 at room temperature for 30 minutes, achieving mortality rates of around 95%. The mutated spores were washed three times with 0.1% Triton X-100 and centrifuged at 3000 rpm at 15° C. for 2 minutes. Petri dishes containing Sutter IV solid medium supplemented with 0.1% Triton X-100 were seeded with the mutated spores and incubated at 25° C. for 4 days to obtain isolated colonies.

The strategies employed for selecting lycopene-overproducing (−) strains of B. trispora were as follows: (i) the use of trisporic acids and (ii) the color intensity of the colony. Selection of lycopene-producing mutants by addition of trisporic acids consisted of placing filters impregnated with trisporic acids over the colonies obtained from mutated spores. The trisporic acids were obtained from a mixed culture of the (+) and (−) strains of B. trispora. The colonies plus filters were incubated at 25° C., and it was observed that the lycopene-producing mutants acquired a deep red color, in contrast to the producers of β-carotene which were colored orange. Applying this method with the CMA3 (−) strain, the LMA1 (−) strain was selected (Scheme 2). Selection of lycopene-producing mutants as a function of the color intensity of the colony was carried out in the following way: The CMA1 (−) strain (producer of β-carotene; see Scheme 2) was mutated and the mutated spores were grown on plates of YEPDA solid medium. Next, those colonies that possessed a deeper yellow-orange color than the CMA1 (−) parent strain were selected. In this way 2 colonies with a deep yellow-orange color were isolated (designated CMB1 (−) and CMB2 (−))

Phylogeny of the (−) strains of B. trispora obtained from B. trispora VKPM F-208 (−) using methods of mutation and selection. UV: ultraviolet; SN: natural selection; NTG: N-methyl-N'-nitro-N-nitrosoguanidine; EMS: ethylmethane sulfonate.

Selection of lycopene-overproducing mutants of B. trispora (+) was effected by growing mutated spores in Petri dishes containing Sutter IV solid medium supplemented with 0.1% imidazole. Next, a portion of each of the colonies was transferred to a dish of PDA in which B. trispora (−) had previously been seeded. The level of lycopene production in solid medium was determined as a function of the intensity of coloration in the zone of intersection of the colony of the (+) strain with that of the (−) strain. In this way the B. trispora CPA1 (+) strain was selected (Scheme 3), which gave rise to a higher yield of lycopene in mixed solid cultures with a series of (−) strains. The level of production of the B. trispora CPA1 (+) strain was then analyzed in mixed culture in liquid medium.

The system of symbols employed for designating the selected strains is as follows:
CM: Carotene minus (−).
LM: Lycopene minus (−).
CP: Carotene plus (+).
LP: Lycopene plus (+).

The relationship between parent generations follows alphabetical order: A is the parent of B, B is the parent of C, and so on. The number after the letters corresponds to the number of the mutant. For example, the designation CMA1 (−) signifies that it is a carotene-producing strain (C), minus (M), parental of CMB and mutant number 1. Similarly, CMA1 (−), CMA2 (−), CMA3 (−) and CMA4 (−) correspond to mutants 1, 2, 3 and 4 of the same generation.

Phylogeny of the B. trispora (+) strains obtained from B. trispora VKPM F-117 (+) using methods of mutation and selection. UV: ultraviolet; SN: natural selection; NTG: N-methyl-N'-nitro-N-nitrosoguanidine; EMS: ethylmethane sulfonate.

The (+) and (−) strains of B. trispora selected in solid medium were fermented in a flask with the aim of determining the level of production of lycopene in liquid medium and mixed culture. For this, separate flasks of inoculum were seeded with the strains B. trispora CPA1 (+) and B. trispora CMB2 (−) and then mixed fermentation of both strains was effected in a flask. At the start of fermentation (0-50 hours) an inhibitor of the enzyme lycopene cyclase was added with the aim of blocking the biosynthetic pathway at the lycopene level (for example imidazole at a concentration of 0.7-0.8 g/l). At the end of fermentation (about 6 days), the mycelium of *B. trispora* was lyzed by vortex agitation, the lycopene was extracted with organic solvents (e.g. acetone) and its concentration and purity were determined by HPLC. The yields obtained were 3.0 g/l. The same type of fermentation was carried out with the strains *B. trispora* CPA1 (+) and *B. trispora* LMA1 (−), except that in this case it was not necessary to add an inhibitor of the enzyme lycopene cyclase. The yields obtained with these strains in mixed culture were 1.2 g/l.

The CPA1 (+) and CMB2 (−) strains were cultivated in a semi-commercial fermenter with the aim of determining the lycopene yield. For this, they were grown separately in flasks, were transferred separately to intermediate growing tanks and finally they were fermented together. Between 25 and 35 hours of fermentation, imidazole was added as inhibitor of the enzyme lycopene cyclase. The fermentation was incubated for 100-140 hours. The average value of lycopene yield obtained in a series of different fermentations of the CPA1 (+) and CMB2 (−) strains was 3.4 g/l.

The CPA1 (+) and LMA1 (−) strains were cultivated in a semi-commercial fermenter with the aim of determining the lycopene yield without addition of inhibitors of the enzyme lycopene cyclase. Fermentation was carried out as indicated previously for the CPA1 (+) and CMB2 (−) strains, but without adding imidazole. The average value of lycopene yield obtained in a series of different fermentations of the CPA1 (+) and LMA1 (−) strains was 1.6 g/l.

A higher yield in this fermentation stage is obtained by controlling the age of the vegetative stages of growth of the strains of *B. trispora*. Thus, the cultures used as inoculum have an age of 30-60 hours, preferably of 48 hours, both for the (+) and the (−) strains, but varying the number of spores seeded: 800-1000 spores/ml and 40 000-60 000 spores/ml, respectively. Incubation is carried out at about 25° C. with 0.1% v/v of each inoculum seeded in the primary culture phase. The age of said primary cultures varies in the range 30-60 hours, preferably 36-48 hours, at temperatures in the range 26-28° C. Then the (+)/(−) primary phases are mixed in the ratio 1/10 v/v and the fermenters are seeded 10-20% v/v with the mixture of said phases.

In view of the intracellular characteristics of the carotenoid component biosynthesized in the fermentation, the method of recovery from the culture medium, prepared as claimed in the usual methods, involves as a first stage the separation of the biomass from the culture medium. This separation can be effected by the established methods of filtration, employing the usual technologies with filters, whether belt filters, rotary filters, press filters etc., in which a barrier consisting of the filter cloth separates the biomass and allows the liquid phase without biomass to pass, or centrifugation, in which, by utilizing the density difference between the culture medium and the biomass (normally of higher density), a machine such as a centrifugal separator, decanter or the like is employed, in which the heavy phase becomes concentrated and separates from the liquid phase with the least possible quantity of biomass. One of the objectives of this stage is to reduce losses and optimize the characteristics of each phase, achieving the greatest quantity of biomass with the highest content of dry residue and eliminating most of the fermentation medium, with the smallest quantity of active material.

The resulting wet mycelium contains more than 95% of the carotenoids produced in fermentation, preferably more than 97% and more preferably more than 99%. The content of carotenoids in the aqueous phase is therefore less than 5%, preferably less than 3% and more preferably less than 1%. With this wet mycelium it would be possible, by means of the subsequent stages, to separate the lycopene. However, it has been found that, in connection with fermentation, this mycelium still has a relatively high percentage of lipophilic components, between 15 and 20% (fatty acids and oils), which cause problems of purification in later stages, so it becomes necessary to introduce a stage of purification of the biomass at this point. The purification stage involves resuspending the biomass in alcohol: methanol, ethanol, propanol, isopropanol, or any other alcohol in which the solubility of lycopene is very low, to a sufficient extent to achieve maximum purification of the lipid components. Thus, the wet mycelium is resuspended with a quantity of alcohol ranging from 1 ml/g to 10 ml/g of wet mycelium. The temperature of resuspension varies between 0° C. and the boiling point of the alcohol, preferably between 10 and 50° C. The contact time is in the range from 5 minutes to 24 hours. The alcoholic resuspension thus prepared is filtered or centrifuged, so that the solids content in the filtrate or clarified liquid is practically zero. The resulting wet mycelium, which will contain alcohol plus water in varying proportions, contains more than 93% of the carotenoids produced in fermentation, preferably more than 95% and more preferably more than 97%.

In the supernatant or filtrate, which contains residues of culture medium and alcohol, the carotenoids content is less than 2%, preferably less than 1%, relative to the initial culture medium. This treatment with alcohol makes it possible to remove a number of alcohol-soluble lipophilic substances, in varying amounts depending on the characteristics of the culture medium used, effecting a pre-purification which will make it possible to obtain a crystalline final product of high purity. Furthermore, by removing a varying proportion of water from the initial wet mycelium, the subsequent drying process is greatly facilitated. By mixing the culture medium directly with the alcohol and maintaining a minimum contact time, a purification effect is achieved equivalent to that described previously, so that the process is simplified by the elimination of one operation of solid-liquid separation. The culture medium/alcohol ratio can vary from 1/0.5 to 1/5, and is preferably between 1/1 and 1/3. The temperature of the mixture varies between room temperature and the boiling point of the mixture, and preferably between room temperature and 60° C.

The dewatered/purified mycelium is dried. Drying can be carried out by the usual batch or continuous methods. The drying temperature varies between room temperature and 150° C., preferably it should not exceed 60° C. and more preferably it should be below 50° C. The drying time depends on the temperature used, and varies between 1 hour and 72 hours. Owing to possible decomposition of these carotenoids by oxidation by atmospheric oxygen, it is best to effect this drying operation in the absence of oxygen, either under a nitrogen atmosphere or at least under vacuum. The fact that the carotenoid product is intracellular means that conditioning of the purified biomass is required, either by drying plus milling, drying plus disintegration or disintegration of the biomass, which promotes mixing with solvents and facilitates solvent extraction. So that the solvent has good access to the carotenoid to be extracted, a prior operation of breaking of the mycelium is necessary, to maximize the area of contact. The optimum particle size of the dry, broken mycelium must be less than 3 mm, preferably less than 1 mm and more preferably less than 0.5 mm.

Milling can be carried out on the dry product, by means of mechanical systems with swiveling or fixed parts: hammers, screens, etc., by passage through rotating cylinders pressing on one another (compaction or extrusion). It is also possible to effect drying and milling in a single stage by means of a flash (instantaneous) drying system in a jet mill, where the wet product is fed to a recirculating gas stream at high temperature, in such a way that the residence time is the minimum to vaporize the content of liquid components, and the product is transported, as the densities vary, to a cyclone where it is recovered. During the drying time and in the drying path, there is also an effect of homogenization as the particles impinge on the walls.

Various organic solvents can be used for extracting the lycopene from a mycelium conditioned in the manner described. This invention will refer to the use of solvents of foodstuff grade that are regarded as natural, such as acyl esters, preferably ethyl, propyl, isopropyl, butyl or isobutyl acetates, which combine reasonably high solubility for the carotenoid components with their compatibility as solvents included in the Group of Class III of the ICH. These solvents are permissible both at national and at community level, in the pharmaceutical and in the foodstuffs field (RDL12/04/90 and RDL16/10/96). As claimed in the ICH, the residual solvents content must be below 5000 ppm, preferably below 1000 ppm and more preferably below 100 ppm, based in each case on the dry matter of the liquid mixture. The extraction temperature varies between room temperature and the boiling point of the solvent, preferably between 50° C. and 80° C. The extraction time will be the minimum necessary to achieve dissolution, between 1 second and 1 hour, preferably between 1 minute and 15 minutes. The quantity of solvent used depends on the temperature and on the carotenoids content of the mycelium, varying between 5 ml/g and 30 ml/g of biomass. The number of extractions varies from 1 to 3. The quantity of carotenoids extracted is greater than 85%, preferably greater than 90% and more preferably greater than 95%.

Once obtained, the carotenoid-rich extract must be concentrated to a defined volume. The final concentration of carotenoids in the solvent after concentrating is preferably between 10 and 50 g/l. The temperature of concentration must be below 80° C., preferably below 70° C. and more preferably below 50° C. Once the extract has been concentrated to the required volume it is necessary to add an insolubilizer of the carotenoids, specifically an alcohol and more specifically methanol, ethanol, propanol, isopropanol or any other alcohol in which the solubility of the lycopene is very low, so that the yield of crystalline lycopene increases considerably. Addition of the alcohol also has a purifying effect. The crystallization time varies between 15 min and 24 hours, preferably between 1 h and 12 h and more preferably between 3 and 8 hours. The crystallization temperature must be below 25° C., preferably below 5° C.

Separation of the crystals from the crystallization liquor can be effected by filtration or centrifugation, displacing the crystallization liquor in which the crystals are immersed by washing with the same alcohol as employed for insolubilization. The crystals obtained are dried under vacuum at room temperature for at least 1 h until a residual solvents content is obtained that meets the specifications laid down by the legislation mentioned earlier and which, in the case of lycopene, stipulates a loss on drying of less than 0.5%.

The purity of the crystals obtained corresponds to a titer above 95%, determined by spectrophotometry by reading the absorption at 472 nm of a solution of the crystals in n-hexane (E1% 1 cm=3450), with a content of other carotenoids below 3%. The content of cis lycopene is below 3%.

The method of this invention is especially suitable for the recovery of crystalline lycopene from a microbial source, preferably algae, fungi or yeasts, more preferably from fungi of the Mucorales order, and more preferably *B. trispora*. The exceptional purity achieved for the crystals obtained by the present methodology and the use of solvents that are regarded as natural means that these crystals can be used. in the food, pharmaceutical or cosmetics industry.

The crystalline product obtained by the methodology described in this invention can be packed in opaque containers which prevent photodegradation of the product, in the absence of oxygen (inert atmosphere or vacuum) to prevent oxidation and at temperatures between 0 and 5° C. The product, properly packed, can be handled and marketed "as is". However, it is advisable to increase its stability by subsequent stages of formulation or finishing, involving the addition of antioxidants that make it possible to obtain a finished product with a shelf life greater than 6 months when properly packed.

Another essential object of this invention is a method of preparation of lycopene that includes its formulation in various presentations as a function of the characteristics of the application for which the lycopene is to be used. A first application, called microcrystalline suspension of lycopene in vegetable oil, consists of premixing of the aforesaid crystalline lycopene with a variable amount of vegetable oil. The type of vegetable oil can be very varied, the commonest though not the only ones being sunflower oil, olive oil, corn oil, soya oil, cottonseed oil, etc. The dosage of lycopene will be a function of the final strength required, the commonest values being suspensions with a lycopene content between 5 and 60%, preferably between 10 and 30%. To increase the stability of the mixture, the usual liposoluble antioxidants are added, such as natural tocopherols, and preferably D,L-alpha-tocopherol. The proportion of this compound varies between 0.2 and 15% relative to the weight of lycopene, preferably between 0.5 and 5%. For the formulations that contain lycopene to have a satisfactory physiological activity, it is necessary to reduce the size of the lycopene crystals. This is achieved with the usual milling systems that are suitable for liquid mixtures. A special object of this invention are ball mills that permit reduction of the size of the crystals below 10 microns, preferably below 5 microns, and even more preferably below 2 microns, using microspheres with a diameter between 0.5 and 0.75 mm. Nevertheless, the crystal size can vary as claimed in the particular application of the suspension, employing appropriate spheres and milling conditions in each case. This crystal size will also determine the rheological properties of the mixture, especially its viscosity, which can also be adjusted as claimed in requirements. These microcrystalline suspensions of lycopene in oil are suitable for applications of lycopene in lipophilic environments: margarine, butter, creams, etc.

A second application, called cold-water-dispersible (CWD) lycopene formulation, is based on dissolution of the lycopene in an organic solvent and its subsequent microencapsulation in modified starches. The solvents that are most suitable for effecting this dissolution, as this molecule exhibits high solubility, are chloroform, benzene, toluene, etc. Methylene chloride is especially suitable. However, owing to the halogenated character of the latter it is possible to use food-grade solvents that are regarded as natural, such as acyl esters, preferably ethyl, propyl, isopropyl, butyl, isobutyl and other acetates, which combine reasonably high solubility for the carotenoid components with their compatibility as solvents included in the Group of Class III of the ICH. The concentration of lycopene in the organic solvent can vary between 1 and 50 g/l, preferably between 10 and 30 g/l. The dissolution temperature can vary between room temperature and the boiling point of the solvent, preferably between 20 and 130° C. The fact that the percentage of cis lycopene is a function of the temperature/time ratio in the operation of dissolution of the lycopene in the organic solvent means that if we wish to obtain a product with a low content of this isomer, either a low dissolution temperature is used, or otherwise a very short dissolution time. Thus, to achieve low levels of cis, if the solvent employed is methylene chloride, dissolution can be carried out at 20-35° C. for a time of between 1 and 15 minutes. If, on the other hand, the solvent is isobutyl acetate, dissolution will preferably be effected between 70 and 130° C. for a few seconds. However, if the levels of cis isomer are not relevant, dissolution can be carried out without restriction on its conditions other than attainment of total solubility at the molecular level of the lycopene in the solvent employed. To increase the stability of the final formulation, one or a mixture of several antioxidants are dissolved together with the lycopene in the organic solvent; these antioxidants are preferably those such as tocopherol, ascorbyl palmitate, etc., each of them in a proportion between 1 and 30%, preferably between 10 and 20%, relative to the weight of lycopene. It is also possible to incorporate vegetable oil in the mixture: sunflower oil, olive oil, corn oil, soya oil, cottonseed oil, etc., for the purpose of promoting dissolution of the lycopene, and imparting additional stability to the preparation. The lycopene/oil ratio can vary between 10/1 and 1/10.

The solution of lycopene thus obtained is mixed and emulsified with an aqueous solution that contains an emulsifying agent, for example modified starch, more concretely esters derived from starch, preferably octenyl succinates derived from starch of various molecular weights, and especially, but not exclusively, Purity Gum 2000 ® from National Starch or Cleargum CO 01® from Roquette, and a microencapsulating agent, consisting for example of modified starch, more concretely esters derived from starch, preferably octenyl succinates derived from starch of various molecular weights, and especially, though not exclusively, HiCap 100® or Capsul® from National Starch. The proportions in which the emulsifying agent and the microencapsulating agent are mixed can vary between 5/95 and 95/5, preferably between 25/75 and 75/25, more preferably between 40/60 and 60/40. The water content of each of the components of the mixture of emulsifying agent and microencapsulating agent is variable, and can be between 1 and 30%, preferably between 5 and 20%, and more preferably 10%. The mixture of aqueous and organic phases is emulsified and the emulsion obtained is homogenized employing pressure-differential homogenization systems of the Mantón Gaulin or Microfluidizer type, as commonly used, and preferably by homogenization by tangential friction, for example with an emulsifier of the Ultraturrax type for a time that varies as a function of the energy supplied by the equipment and the volume of mixture to be emulsified, with the aim of obtaining an average micelle size smaller than 10 microns, preferably smaller than 2 microns and more preferably between 0.1 and 1 micron.

Once the emulsion has formed, evaporation of the organic solvent is effected, preferably by vacuum distillation at a temperature below 50° C. As evaporation of the solvent proceeds, microcrystallization of the lycopene takes place in the starch matrix. Once the solvent has evaporated, evaporation continues, with successive additions of water until a residual solvents content is obtained that complies with the specifications on maximum concentration laid down by the legislation and a dry residue that is suitable for the type of drying that is to be applied to this liquid mixture. Suitable values of dry matter in the suspension of microencapsulated lycopene are between 1 and 30%, and preferably between 10 and 20%.

In accordance with the present invention, it is found that both the method of drying by high-temperature pulverization (atomization) and the method of fluidized-bed pulverization (granulation) are suitable for drying the aqueous suspension of lycopene obtained. Another alternative would be freeze-drying. As claimed in the method of drying by atomization, suitable inlet temperatures of the drying air would be between 100 and 200° C. whereas the outlet temperatures would be between 60 and 120° C. The atomized product has a particle size between 10 and 100 microns. With the aim of increasing the particle size and reducing the area available, and thus increasing the product's oxidation resistance, the atomized product can be agglomerated by pulverization of a solution of one of the modified starches used in the formulation, or the suspension of microencapsulated lycopene itself, within a fluidized bed of said atomized product, which makes it possible to attain particle sizes that vary between 50 and 500 microns, preferably between 200 and 300 microns.

The method of granulation involves the use of a fluidized-bed granulator in which seed material is placed, which can be a typical inert material, such as particles of sugar, or fine powder of the actual material to be dried, obtained in previous granulation processes or in a spray-drying process. The particles are kept in motion by means of air, and the temperature of the bed is maintained between 30 and 90° C., preferably between 50 and 80° C. The suspension of microencapsulated lycopene is sprayed by means of air preheated to a temperature between 20 and 140° C. within the fluidized bed, at a rate that ensures that the particles that will be coated do not become too wet and do not form lumps. The granulated product has a particle size between 100 and 2000 microns, preferably between 100 and 800 microns and more preferably between 100 and 300 microns. Once pulverization by one or other method has been completed, the particles can be coated. This coating can be effected with approximately 0.5-10% in dry weight of aqueous solutions of various sugars or even of one or a mixture of the starches that make up the formula that is the object of the present invention.

Deposit of Microorganisms in Accordance with the Treaty of Budapest

The strains of *Blakeslea trispora* have been deposited, in accordance with the provisions of the Treaty of Budapest, in the Russian National Collection of Industrial Microorganisms (VKPM), GNII Genetika, Dorozhny Proezd 1, Moscow 113545 (Russia), with the following numbers and dates: VKPM F-117 on 12.21.1979, VKPM F-208 on 12.20.1979, VKPM F-551 on 11.19.1992, VKPM F-674 on 11.19.1992, VKPM F-726 on 01.21.1997, VKPM F-727 on 01.21.1997, VKPM F-736 on 10.07.1997, VKPM F-741 on 01.28.1998, VKPM F-744 on 01.28.1998 and VKPM F-816 on 12.13.2000.

The following examples describe the present invention in detail and without limitation.

EXAMPLE 1

Strategies for Mutation of the (+) and (−) Strains of *B. trispora*

Firstly a mutagenic method was developed for the (+) and (−) strains of *B. trispora*, for which the following were analyzed: (i) various types of mutagenic agents, (ii) concentration of the mutagen, (iii) concentration of spores, (iv) incubation pH, and (v) treatment time. In this way, ethylmethane sulfonate (EMS) and N-methyl-N'-nitro-N-nitrosoguanidine (NTG) were selected as mutagenic agents.

The suspensions of spores to be mutated were obtained from slants with YpSs medium, which has the following composition: yeast extract 4 g/l, soluble starch 15 g/l, $K_2HPO_4$ 1 g/l, $MgSO_4.7H_2O$ 0.5 g/l and agar 15 g/l, at a final pH of 5.8. The spores were resuspended by adding 10 ml of a 0.1% solution of Triton X-100 to each slant. The mycelium residues were removed by filtration through a nylon filter with pore size of 20 μm. The concentration of spores in the suspension was about $10^6$ spores/ml.

The method of mutation with EMS consisted of incubating $10^6$ spores/ml in a solution of EMS at 3% in 0.1 M sodium phosphate buffer pH 7.0 at room temperature for 60 minutes, achieving mortality rates of around 99%. The mutated spores were washed three times with 0.1% Triton X-100, centrifuging at 15° C. and 3000 rpm for 2 minutes.

The method of mutation with NTG consisted of incubating $10^6$ spores/ml in a solution that contained 250 82 g/ml of NTG and 0.1 M sodium citrate buffer pH 5.0 at room temperature for 30 minutes, achieving mortality rates of around 95%. The mutated spores were washed three times with 0.1% Triton X-100, centrifuging at 15° C. and 3000 rpm for 2 minutes.

The mutated spores were used for seeding Petri dishes that contained Sutter IV solid medium supplemented with 0.1% Triton X-100. The composition per liter of the Sutter IV medium is as follows: 40 g glucose, 4 g L-asparagine, 10 g $KH_2PO_4$, 40 ml of solution of trace elements 50x, and 30 g of agar. The solution of trace elements 50x is made up of: 25 g/l of $MgSO_4.7H_2O$, 1.82 g/l of $CaCl_2.2H_2O$, 0.05 g/l of thiamine, 0.1 g/l of citric acid, 0.075 g/l of $Fe(NO_3)_3.9H_2O$, 0.05 g/l of $ZnSO_4.7H_2O$, 0.17 g/l of $MnSO_4.H_2O$, 0.025 g/l of $CuSO_4.5H_2O$ and 0.025 g/l of $NaMoO_4.2H_2O$. The seeded dishes were incubated at 25° C. for 4 days to obtain isolated colonies.

EXAMPLE 2

Figure 1:
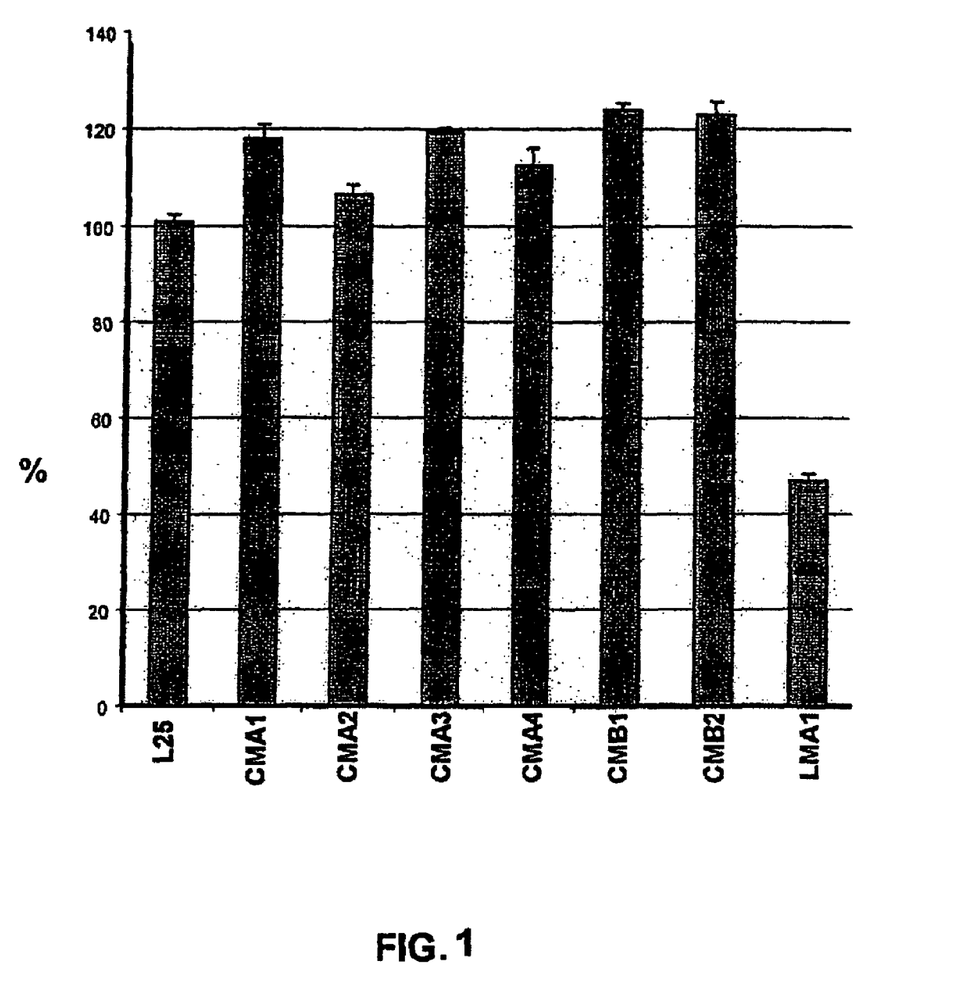
FIG. 1. Production of lycopene by mixed fermentation of the *B. trispora* CPA1 (+) strain in a flask with each of the following strains of *B. trispora* (−): L25, CMA1, CMA2, CMA3, CMA4, CMB1, CMB2 and LMA1. Except in CPA1 (+)/LMA1 (−) mixed fermentation, imidazole was added as inhibitor of the enzyme lycopene cyclase. Ordinate: % of production with control strain L25 (−) (VKPM F-744).

Strategies for Selecting Mutants of *B. trispora* (−) that are Lycopene Overproducers This example describes strategies for selecting strains of *B. trispora* (−) that are lycopene overproducers, based on (i) the use of trisporic acids and (ii) the color intensity of the colony. FIG. 1 shows the phylogeny of the *B. trispora* (−) strains used in the present invention.

Selection of lycopene-producing mutants by adding trisporic acids was effected by placing sterile filters about 0.6 mm in diameter, impregnated with trisporic acids, on the colonies obtained from mutated spores. The trisporic acids were obtained by extracting the supernatant from a mixed culture of the (+) and (−) strains of *B. trispora* with one volume of chloroform after acidifying the sample to pH 2. The organic fraction was extracted with one volume of a 4% solution of sodium bicarbonate, collecting the aqueous phase, which was acidified and extracted with chloroform again. Next, the chloroform was evaporated to dryness and the residue, enriched with trisporic acids, was dissolved in ethanol. The trisporic acids were quantified by measuring the absorbance at 325 nm and assuming an absorption coefficient of 70 ml×$mg^{-1}$×$cm^{-1}$ (Sutter R. P., Capage D. A., Harrison T. L., Keen W. A. 1973. J. Bacteriology 114:1074-1082).

The sterile filters were incubated in a solution of 1.2 mg/ml of trisporic acids in ethanol and were then left to dry at room temperature in sterile conditions. Next, the filters were placed on the mutant colonies previously grown for 4 days at 25° C. The dishes were incubated at 25° C. for a further 3 days, and it was observed that the lycopene-producing mutants became a deep red in color, in contrast to the producers of β-carotene whose color was orange.

Applying this method with the CMA3 (−) strain, the mutant LMA1 (−) was obtained (FIG. 1), which might have a mutation in the caRP gene, which codes for the enzyme lycopene cyclase and therefore, instead of producing β-carotene, should accumulate the intermediate lycopene during the process of fermentation of carotenoids. Therefore the LMA1 strain is able to produce lycopene without the need to add specific inhibitors of lycopene cyclase activity (example 5).

Selection of lycopene-producing mutants in relation to the color intensity of the colony was effected as follows: The CMA1 strain (producer of β-carotene; see FIG. 1) was mutated as described in example 1. The mutated spores were seeded on dishes of YEPDA solid medium (bacto-peptone 20 g/l, yeast extract 10 g/l, glucose 20 g/l and agar 20 g/l, to a final pH of 6.0), and were incubated at 25° C. for 24 hours and then at 20° C. for 48-72 hours. Finally, those colonies with a deeper yellow-orange color than the CMA1 (−) parent strain were selected. In this way, 2 colonies were isolated with deep yellow-orange color (designated CMB1 (−) and CMB2 (−)). The CMB1 and CMB2 strains might be overproducers of lycopene in mixed fermentations with addition of specific inhibitors of lycopene cyclase activity (for example imidazole; example 4).

EXAMPLE 3

Strategies for Selecting Mutants of *B. trispora* (+) that are Overproducers of Lycopene Selection of lycopene-overproducing mutants of *B. trispora* (+) was effected using mutated spores in the manner described in example 1. These spores were seeded on Petri dishes that contained Sutter IV solid medium supplemented with 0.1% imidazole and were incubated at 25° C. for 7 days to obtain isolated colonies. Next, a portion from each of the colonies was transferred to a dish of PDA on which *B. trispora* (−) had been seeded previously. The distance between the seeding points of the (+) and (−) strains must be approximately 2 cm. The level of production of lycopene in solid medium is estimated from the intensity of coloration in the zone of intersection of the colony of the (+) strain with that of the (−) strain. In this way the *B. trispora* strain CPA1 (+) was selected, and this gave rise to a higher yield of lycopene in mixed solid cultures with a series of (−) strains. The level of production from the *B. trispora* strain CPA1 (+) was then analyzed in mixed culture in a liquid medium as described in examples 4 and 5. Scheme 3 shows the phylogeny of the *B. trispora* (+) strains used in the present invention.

EXAMPLE 4

Method of Production of Lycopene in a Flask by Mixed Culture of the (+) and (−) Strains of *B. trispora* by Adding Inhibitors of the Enzyme Lycopene Cyclase The (+) and (−) strains of *B. trispora* selected as described in examples 1, 2 and 3 were fermented in a flask with the aim of determining the level of production of lycopene in a liquid medium and mixed culture. For this, an inoculum medium was prepared with the following composition per liter: 23 g of soya flour, 47 g of maize flour, 0.5 g of $KH_2PO_4$, 0.002 g of thiamine hydrochloride and pH adjusted to 6.3. The CPA1 (+) strain of *B. trispora* was seeded in 500-ml flasks containing 67 ml of medium at the rate of 103 spores per ml. The CMB2 (−) strain of *B. trispora* was seeded in 500-ml flasks containing 100 ml of medium at a rate of 104 spores per ml. Both types of inoculum were incubated at 25° C. and 250 rpm for 44 hours.

On completion of incubation, the inocula of the (+) and (−) strains were mixed in the ratio 1/10 (v/v), and the mixture was used for inoculating 250-ml flasks containing 20 ml of fermentation medium at a rate of 4 ml of the mixture of strains per flask. These flasks were incubated at 25° C. and 250 rpm for 5-6 days. The fermentation medium used had the following composition per liter: 44 g of soya flour, 19 g of maize flour, 5.5 g of $KH_2PO_4$, 0.002 g of thiamine hydrochloride, 100 ml of vegetable oil, and pH adjusted to 7.5. The medium was distributed in 250-ml flasks, which were inoculated with 20% of a mixture of the (+) and (−) strains of B. trispora. Between the 0th and the 36th hours of fermentation, an inhibitor of the enzyme lycopene cyclase was added with the aim of blocking. the biosynthetic pathway at the lycopene level (for example, 0.75 mg/ml of imidazole). The flasks were incubated at 25° C. and 250 rpm for 6 days. At the end of fermentation, a mixture of fermentation medium, glass beads and methylene chloride/methanol (1/1) was prepared. The mycelium of B. trispora was lyzed by vortex agitation, releasing the intracellular lycopene. The lycopene extracted with the methylene chloride/methanol mixture (ratio 1:1) was diluted in acetone. The concentration and purity of the lycopene were determined using reversed-phase HPLC.

The yield obtained in mixed fermentations of the strains B. trispora CPA1 (+) and B. trispora CMB2 (−) was 3 g/l of lycopene in the presence of imidazole (FIG. 1).

EXAMPLE 5

Method of Production of Lycopene in the Flask by Mixed Culture of the B. trispora CPA1 (+) and B. trispora LMA1 (−) Strains without Addition of Inhibitors of the Enzyme Lycopene Cyclase The strains of B. trispora LMA1 (−) and CPA1 (+) selected as described in examples 1, 2 and 3 were fermented in a flask with the aim of determining the level of production of lycopene in liquid medium and mixed culture. For this, inocula were prepared from the (+) and (−) strains and fermentation was carried out in a flask as described in example 4. The difference is that in this case the chemical inhibitor of lycopene cyclase activity was not added. At the end of fermentation, production of lycopene was evaluated as described in example 4.

Figure 2:
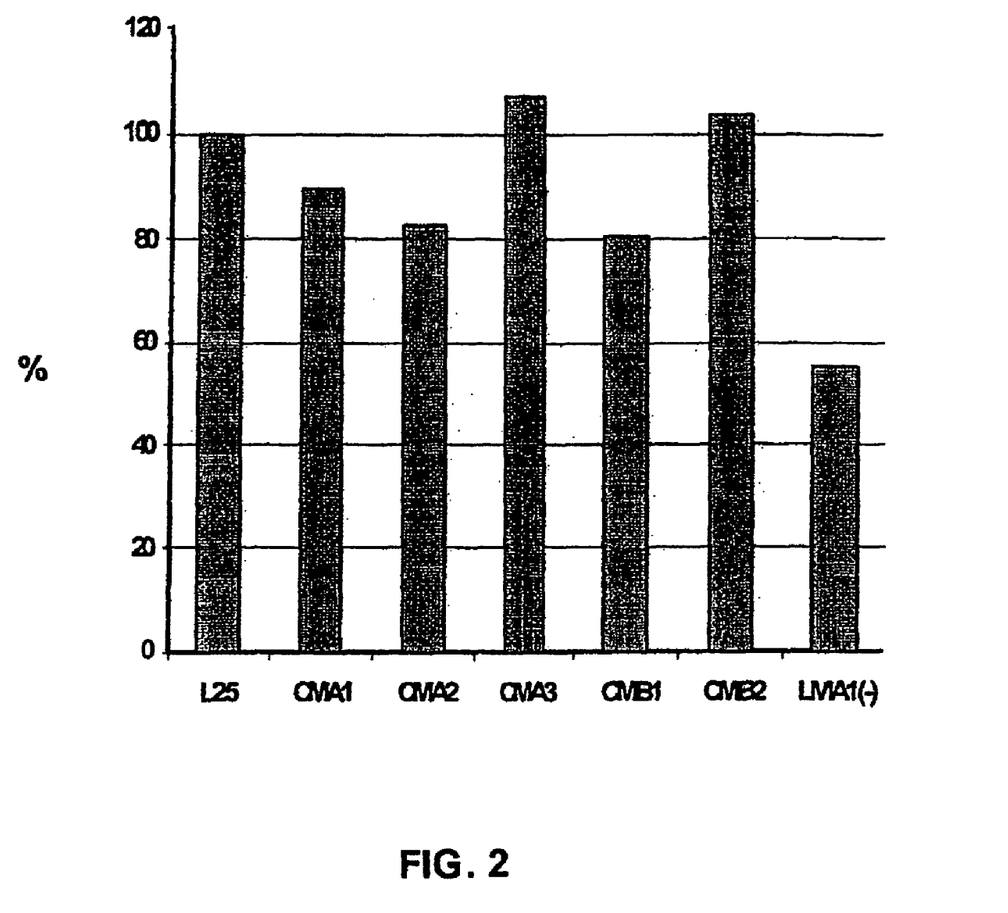
FIG. 2. Production of lycopene by mixed fermentation of the *B. trispora* CPA1 (+) strain in a fermenter with each of the following strains of *B. trispora* (−): L25, CMA1, CMA2, CMA3, CMB1, CMB2 and LMA1. Except in CPA1 (+)/LMA1 (−) mixed fermentation, imidazole was added as inhibitor of the enzyme lycopene cyclase. Ordinate: % of production with control strain L25 (−) (VKPM F-744).

The yields obtained by mixed fermentation of the strains B. trispora CPA1 (+) and B. trispora LMA1 (−) were 1.2 g/l of lycopene in the absence of imidazole (FIG. 2).

EXAMPLE 6

Method of Production of Lycopene in a Semi-commercial Fermenter by Mixed Culture of the (+) and (−) Strains of B. trispora with Addition of Inhibitors of the Enzyme Lycopene Cyclase The CPA1 (+) and CMB2 (−) strains of B. trispora selected as described in examples 2 and 3 were cultivated in a semi-commercial fermenter with the aim of determining the lycopene yield. For this, an inoculum was prepared with the following composition per liter: 23 g of soya flour, 47 g of maize flour, 0.5 g of $KH_2PO_4$, 0.002 g of thiamine hydrochloride, and with its pH adjusted to 6.3. The (+) and (−) strains were seeded separately in 2000-ml flasks containing 500 ml of medium and were incubated at 25° C. and 250 rpm for 44-48 hours.

Each of the strains was transferred to an intermediate growing tank containing a culture medium with the following composition per liter: 29 g of Pharmamedia, 47 g of maize flour, 0.5 g of $KH_2PO_4$; 0.002 g of thiamine hydrochloride and 1 g of antifoaming agent, and with its pH adjusted to 6.0. After incubating for 36-48 h, the (+) and (−) strains were mixed in a 1/10 ratio and 20% of the mixture was used for seeding the fermentation base medium, which had the following composition per liter: 44 g of soya flour, 19.25 g of maize flour, 0.55 g of $KH_2PO_4$, 3.36 g of $Na_2HPO_4$, 0.184 g of $NaH_2PO_4$, 0.0022 g of thiamine hydrochloride, 100 g of vegetable oil and 0.175 g of antifoaming agent, and its initial pH was adjusted to 7.5. The fermentation was incubated for 100-140 hours at a temperature of 25-28° C. with stirring varying between 150 and 250 rpm and aeration of 1-1.5 v/v/m. Between the 25th and 35th hours of fermentation, sterile imidazole was added to a final concentration of 0.75 g/l.

Evaluation of the concentration and purity of the lycopene at the end of fermentation was carried out as described in example 4. The average value of lycopene yield obtained in a series of different fermentations of the CPA1 (+) and CMB2 (−) strains was 3.4 g/l (FIG. 2).

EXAMPLE 7

Method of Production of Lycopene in a Semi-commercial Fermenter by Mixed Culture of the Strains B. trispora CPA1 (+) and B. trispora LMA1 (−) without Addition of Inhibitors of the Enzyme Lycopene Cyclase The CPA1 (+) and LMA1 (−) strains of B. trispora selected in the manner described in examples 2 and 3 were cultivated in a semi-commercial fermenter with the aim of determining the level of production of lycopene without adding inhibitors of the enzyme lycopene cyclase. For this, an inoculation medium was prepared with the following composition per liter: 23 g of soya flour, 47 g of maize flour, 0.5 g of $KH_2PO_4$, 0.002 g of thiamine hydrochloride, and with its pH adjusted to 6.3. The (+) and (−) strains were seeded separately in 2000-ml flasks containing 500 ml of medium and were incubated at 25° C. and 250 rpm for 44-48 hours.

Each of the strains was transferred to an intermediate growing tank containing a culture medium with the following composition per liter: 29 g of Pharmamedia, 47 g of maize flour, 0.5 g of $KH_2PO_4$; 0.002 g of thiamine hydrochloride and 1 g of antifoaming agent, and with its pH adjusted to 6.0. After incubating for 36-48 h, the (+) and (−) strains were mixed in a 1/10 ratio and 20% of the mixture was used for seeding the fermentation base medium, which had the following composition per liter: 44 g of soya flour, 19.25 g of maize flour, 0.55 g of $KH_2PO_4$, 3.36 g of $Na_2HPO_4$, 0.184 g of $NaH_2PO_4$, 0.0022 g of thiamine hydrochloride, 100 g of vegetable oil and 0.175 g of antifoaming agent, and its initial pH was adjusted to 7.5. The fermentation was incubated for 100-140 hours at a temperature of 25-28° C. with stirring varying between 150 and 250 rpm and aeration of 1-1.5 v/v/m.

Evaluation of the concentration and purity of the lycopene at the end of fermentation was carried out as described in example 4. The average value of lycopene yield obtained without addition of imidazole in a series of different fermentations of the CPA1 (+) and LMA1 (−) strains was 1.6 g/l (FIG. 2).

EXAMPLE 8

Method of Recovering Lycopene by Resuspension of the Biomass in Alcohol

Three liters of fermentation medium were harvested, corresponding to a biosynthesis process in which the biosynthetic pathway was interrupted at the lycopene level. The titer of the medium was 3 g of lycopene per liter. The biomass of this culture medium was recovered by filtration with a Buchner funnel (porcelain filter funnel which supports a disk of paper or card which acts as a filtering sheet), obtaining 750 g of wet biomass. The wet biomass was resuspended in 5.2 l of azeotropic isopropanol 85/15 and was stirred for 30 minutes at 45±5° C. Recovery of the purified biomass using a Buchner funnel was repeated. This biomass was dried under vacuum in a stove at a temperature below 45±5° C. for 18 hours, until the content of residual solvents/water was less than 8%. 150 g of dry, purified biomass was obtained with a lycopene content equivalent to an assay value of 5.5%. The dry biomass was milled in a ball mill and a 1 mm screen, obtaining a solid with the same percentage content, which was conditioned to permit solvent extraction.

Extraction was effected by mixing the 150 g of milled biomass with 2500 ml of isobutyl acetate at 70±5° C., continuing stirring for 5 minutes. The spent biomass was separated from the lycopene-rich solvent by filtering on a filter plate. The spent biomass was washed with 300 ml of hot isobutyl acetate on the same filter, mixing the washing solvent with the filtrate. All of the lycopene-rich isobutyl acetate was concentrated under vacuum, keeping the temperature below 45±5° C., until the volume was reduced to 300 ml, whereupon some of the lycopene crystallized. In order to complete crystallization and obtain a purer lycopene, 900 ml of isopropanol was added. Stirring of the mixture was continued, under nitrogen and in the temperature range 0-5° C., for 3 hours. It was filtered in a Buchner funnel, washing the crystals with 25 ml of isopropanol on the Buchner funnel. The crystals were collected and then dried under vacuum, obtaining 6.5 g of lycopene crystals with a spectrophotometric purity of 95%. Neither the presence of other carotenoids, nor of cis lycopene, was detected by HPLC.

EXAMPLE 9

Method of Formulation of Lycopene in Oily Suspension

A laboratory ball mill, type Minizeta 003 from Netzsch, was charged with the following, in this order: microspheres with diameter of 0.5-0.75 mm, 23.5 g of sunflower oil (Koipe), 0.065 g of D,L-alpha-tocopherol (Merck) and the 6.5 g of crystalline lycopene obtained as described in example 8. The mixture was milled at 3000 rpm for 5 minutes, obtaining 25 g of a viscous liquid of a deep reddish-purple color. Spectrophotometric analysis of the oily suspension revealed a lycopene content of 21%. Neither the presence of other carotenoids nor of cis isomers of lycopene was detected by HPLC. The crystals were smaller than 10 microns.

EXAMPLE 10

Method of Recovery of Lycopene by Direct Treatment of the Fermentation Medium with Alcohol 1500 l of lycopene fermentation medium (lycopene strength 2.3 g/l) was mixed directly with 4500 liters of 85/15 isopropanol/water azeotrope. After stirring for 30 min at 45±5° C., the biomass was separated from the liquid using a centrifugal decanter. Around 250 kg of wet, purified biomass was collected.

This biomass, soaked with water and isopropanol, was dried in a rotary dryer under vacuum until the content of residual solvents/water was below 8%. The drying temperature was 45±5° C., and the average residence time in the dryer was 14 hours. 85 kg of dry biomass was obtained with a lycopene content equivalent to a specific concentration of 3.75%.

The dry biomass was extruded in a compactor, Hutt-Compacktor from BEPEX, obtaining a solid with the same specific concentration, which was conditioned to permit solvent extraction.

Extraction was effected by mixing the 85 kg of milled solid with 1650 l of isobutyl acetate. The mixture was heated in line at 60±5° C. for an approximate average contact time of 2 minutes and the spent biomass was separated from the lycopene-rich solvent using a centrifugal decanter. The whole of the lycopene-rich isobutyl acetate was concentrated under vacuum, maintaining the temperature below 45±5° C., until the volume was reduced to 100 l, whereupon a proportion of the lycopene crystallized. To complete crystallization of the lycopene, 300 l of isopropanol was added. The mixture was stirred for 3 h at 0-5° C. It was filtered on a Buchner funnel, collecting the lycopene crystals, which were dried under vacuum at room temperature. 2 kg of product was obtained, with a spectrometric purity of 96%. Neither the presence of other carotenoids nor of cis isomers was detected by HPLC.

EXAMPLE 11

Method of Formulation of Water-dispersible Lycopene Using Isobutyl Acetate as Solvent 3.5 g of lycopene obtained as described in example 10 was resuspended in 410 ml of isobutyl acetate and 0.35 g of D,L-alpha-tocopherol (Merck) was added. The mixture was heated to boiling (114° C.) for 5 minutes, ensuring complete dissolution of the lycopene. At the same time, 12 g of Hi-Cap 100 (National Starch) and 12 g of Purity Gum 2000® (National Starch) were dissolved in 325 ml of demineralized water. The hot organic phase was emulsified for 5 minutes in one stage over the aqueous phase using an Ultraturrax emulsifier from IKA, achieving an average micelle size of 1.2 microns, measured with a Coulter LS230 analyzer. The emulsion was transferred to a vacuum distillation system, adding 600 ml of water, so that the 410 ml of isobutyl acetate was evaporated with approximately 700 ml of water. 203 g of liquid formulation (12.75% of dry matter) was obtained, with a lycopene content of 1.25% (9.8% based on the dry mass). Using HPLC, a content of cis lycopene of 23.3% was detected, but no other carotenoids were detected. This liquid formulation was atomized in a Büchi 190 laboratory atomizer, employing a gas temperature of 190° C. at inlet and 90° C. at outlet, obtaining a powder of a deep red color, with a lycopene content of 8.4% and a water content of 6.5%. Using HPLC, a content of cis lycopene of 23% was detected, but no other carotenoids were detected.

EXAMPLE 12

Method of Formulation of Water-dispersible Lycopene Using Isobutyl Acetate as Solvent 3.5 g of lycopene obtained as described in example 10 was resuspended in 410 ml of isobutyl acetate and 0.35 g of D,L-alpha-tocopherol (Merck), 0.7 g of ascorbyl palmitate (Merck) and 3.5 g of sunflower oil (Koipe) were added. The mixture was heated to boiling (114° C.) for 5 minutes, ensuring complete dissolution of the lycopene. At the same time, 10 g of Hi-Cap 100 (National Starch) and 10 g of Purity Gum 2000® (National Starch) were dissolved in 325 ml of demineralized water. The hot organic phase was emulsified for 5 minutes in one stage over the aqueous phase using an Ultraturrax emulsifier from IKA, achieving an average micelle size of 1.4 microns, measured with a Coulter LS230 analyzer. The emulsion was transferred to a vacuum distillation system, adding 600 ml of water, so that the 410 ml of isobutyl acetate was evaporated with approximately 700 ml of water. 195 g of liquid formulation (13.25% of dry matter) was obtained, with a lycopene content of 1.3% (9.8% based on the dry mass). Using HPLC, a content of cis lycopene of 25% was detected, but no other carotenoids were detected. This liquid formulation was atomized in a Büchi 190 laboratory atomizer, employing a gas temperature of 190° C. at inlet and 90° C. at outlet, obtaining a powder of a deep red color, with a lycopene content of 8.5% and a water content of 6.0%. Using HPLC, a content of cis lycopene of 24.5% was detected, but no other carotenoids were detected.

EXAMPLE 13

Method of Formulation of Water-dispersible Lycopene Using Dichloromethane as Solvent 7.5 g of crystalline lycopene obtained as described in example 10 was resuspended in 500 ml of dichloromethane, adding 0.75 g of D,L-alpha-tocopherol (Merck), and heating the mixture at 35° C. for 5 minutes. At the same time, 27 g of Hi-Cap 100 (National Starch) and 27 g of Purity Gum 2000® (National Starch) were dissolved in 400 ml of distilled water. The organic phase was emulsified for 15 minutes in one stage over the aqueous phase using an Ultraturrax emulsifier from IKA, achieving an average micelle size of 0.4 microns, measured with a Coulter LS230 analyzer. The emulsion was transferred to a vacuum distillation system, adding 600 ml of water, so that the 500 ml of dichloromethane was evaporated with approximately 600 ml of water. 400 g of liquid formulation (13.1% of dry matter) was obtained, with a lycopene content of 1.5% (11.5% based on the dry mass). Using HPLC, a content of cis lycopene of 6.5% was detected, but no other carotenoids were detected. This liquid formulation was atomized in a Büchi 190 laboratory atomizer, employing a gas temperature of 190° C. at inlet and 90° C. at outlet, obtaining a powder of a deep red color, with a lycopene content of 10.6% and a water content of 5.3%. Using HPLC, a content of cis lycopene of 6.4% was detected, but no other carotenoids were detected.

EXAMPLE 14

Method of Formulation of Water-dispersible Lycopene Using Dichloromethane as Solvent 7.5 g of crystalline lycopene obtained as described in example 10 was resuspended in 500 ml of dichloromethane, adding 0.75 g of D,L-alpha-tocopherol (Merck), and heating the mixture at 35° C. for 5 minutes. At the same time, 27 g of Hi-Cap 100 (National Starch) and 27 g of Purity Gum 2000® (National Starch) were dissolved in 400 ml of distilled water. The organic phase was emulsified for 60 minutes in one stage over the aqueous phase using an Ultraturrax emulsifier from IKA, achieving an average micelle size of 0.23 microns, measured with a Coulter LS230 analyzer. The emulsion was transferred to a vacuum distillation system, adding 600 ml of water, so that the 500 ml of dichloromethane was evaporated with approximately 650 ml of water. 350 g of liquid formulation (14.4% of dry matter) was obtained, with a lycopene content of 1.6% (11.4% based on the dry mass). Using HPLC, a content of cis lycopene of 20% was detected, but no other carotenoids were detected. This liquid formulation was freeze-dried in a laboratory unit for 24 hours, obtaining a fluffy powder of a deep red color, with a lycopene content of 10.7% and a water content of 7.4%. Using HPLC, a content of cis lycopene of 15% was detected, but no other carotenoids were detected.

The invention claimed is:

1. Crystalline lycopene having a crystal purity, determined by spectrophotometric absorption of the crystals in n-hexane at 472 nm (E1% 1 cm=3450), greater than 95%, and being free of carotenoids other than lycopene, said crystalline lycopene being obtainable by a process comprising the following steps in succession
   a. Mixing (+) and (−) lycopene overproducer strains of *Blakeslea trispora*, whose ages of vegetative stage of growth has been controlled, in a culture medium biomass in suitable fermentation conditions for producing lycopene;
   b. Treatment of the culture medium biomass of step a) with alcohol and separation of a wet, purified biomass;
   c. Conditioning of the wet, purified biomass by drying and disintegration or breaking;
   d. Solid-liquid extraction of the lycopene contained in the purified biomass with an organic solvent, controlling the temperature and the time of dissolution in function of the organic solvent used;
   e. Concentration of the enriched lycopene extract;
   f. Precipitation/crystallization of the lycopene from the concentrated extract by addition of alcohol to form a crystalline liquor; and
   g. Filtration of crystals of lycopene from the crystalline liquor and drying.

2. A lycopene formulation comprising an oil suspension of the crystalline lycopene of claim 1, having a lycopene crystal size below 10 microns.

3. A lycopene formulation comprising a dispersion in cold water of the crystalline lycopene of claim 1, wherein said crystalline lycopene has been atomized to an average particle size between 10 and 100 microns.

4. A coated particle comprising the lycopene formulation according to claim 3 coated with 0.5-10% in dry weight of a sugar or modified starch from an aqueous solution.

5. A lycopene formulation comprising a dispersion in cold water of the crystalline lycopene of claim 1, wherein said crystalline lycopene has been atomized and agglomerated to an average particle size in the range 50-500 microns.

6. A coated particle comprising the lycopene formulation according to claim 5 coated with 0.5-10% in dry weight of a sugar or modified starch from an aqueous solution.

7. A lycopene formulation comprising a dispersion in cold water of the crystalline lycopene of claim 1, wherein said crystalline lycopene has been atomized and granulated to an average particle size between 100 and 2000 microns.

8. A coated particle comprising the lycopene formulation according to claim 7 coated with 0.5-10% in dry weight of a sugar or modified starch from an aqueous solution.

9. A method for coloring a product comprising providing the crystalline lycopene of claim 1 and incorporating the crystalline lycopene into the product.

10. The method according to claim 9, wherein the product is selected from the group consisting of a food, a pharmaceutical, a cosmetic and a diet supplement.

11. The crystalline lycopene of claim 1 obtained by the process comprising steps a-g.

12. The crystalline lycopene according to claim 1, which is also free of cis lycopene.

13. Process of production of the crystalline lycopene of claim 1 from biosynthetic sources, comprising the following steps in succession:
   a. Mixing (+) and (−) lycopene overproducer strains of *Blakeslea trispora*, whose ages of vegetative stage of growth has been controlled, in a culture medium biomass in suitable fermentation conditions for producing lycopene;
b. Treatment of the culture medium biomass of step a) with alcohol and separation of a wet, purified biomass;
c. Conditioning of the wet, purified biomass by drying and disintegration or breaking;
d. Solid-liquid extraction of the lycopene contained in the purified biomass with an organic solvent, controlling the temperature and the time of dissolution in function of the organic solvent used;
e. Concentration of the enriched lycopene extract;
f. Precipitation/crystallization of the lycopene from the concentrated extract by addition of alcohol; and
g. Filtration and drying.

14. Process according to claim 13, in which the overproducer strains have an age ranging 30-60 h, with a number of spores seeded of 800-1000 spores/ml for (+) strains and 40000-60000 spores/ml for (−) strains, being seeded 0.1% v/v of each inoculum in a primary culture phase.

15. Process according to claim 14, in which the age of primary cultures in the primary culture phase ranges from 30-60 h.

16. Process according to claim 13, wherein in the step a., together with the (+) strains, use is made of *Blakeslea trispora* (−) strains, mutants or transformants derived from them, which produce lycopene.

17. Process according to claim 16, wherein at least 1.6 g/l of lycopene is produced at days 5-6 of culture, in a semi-commercial or pilot fermenter.

18. Process according to claim 13, wherein in the step a., together with the (−) strains, use is made of *Blakeslea trispora* (+) strains, mutants or transformants derived from them, which produce lycopene.

19. Process according to claim 13, when in step a. mixed cultures of strains of *Blakeslea trispora* (−) and (+) or mutants or transformants derived from them, which produce lycopene, are used in the absence of compounds that are inhibitors of lycopene cyclase activity.

20. Process according to claim 13, wherein in step a. mixed cultures of strains of *Blakeslea trispora* (−) and (+) or mutants or transformants derived from them, which produce lycopene, are used in the presence of compounds that are inhibitors of lycopene cyclase activity.

21. Process according to claim 20, comprising the addition of imidazole during the fermentation process, as an inhibitor of lycopene cyclase activity.

22. Process according to claim 21, wherein the imidazole is added between the 0th and 50th hours of fermentation, preferably between the 25th and 35th hours.

23. Process according to claim 21, wherein the concentration of imidazole is maintained between 0.7 and 0.8 g/l, preferably at 0.75 g/l.

24. Process according to claim 20, wherein at least 3.4 g/l of lycopene is produced at days 5-6 of culture, in a semi-commercial or pilot fermenter.

25. Process according to claim 13, wherein
i) inocula of the (+) strain of *B. trispora* are seeded in a range of 800-1000 spores/ml;
ii) inocula of the (−) strain of *B. trispora* are seeded in a range of 10000-60000 spores/ml;
iii) the inocula of the (+) and (−) strains of *B. trispora* are cultivated for at least 48 hours at 25° C.;
iv) phases of primary culture of the (+) strain of *B. trispora* are seeded with at least 0.1% (v/v) of the inoculation phase;
v) phases of primary culture of the (−) strain of *B. trispora* are seeded with at least 0.1% (v/v) of the inoculation phase;
vi) primary phases of the (+) strain of *B. trispora* are cultivated for 36-48 hours at 26° C.;
vii) primary phases of the (−) strain of *B. trispora* are cultivated for 36-48 hours at 28° C.;
viii) primary phases of the (+) and (−) strains of *B. trispora* are mixed in the proportions 1 (+)/10 (−) (v/v);
ix) at least one fermenter is seeded with 10-20% (v/v) of the mixture of the (+) and (−) strains of *B. trispora* described in paragraph viii; and
x) the mixed culture is incubated for 5-6 days at 26° C.

26. Process according to claim 25, wherein at least 3.6 g/l of lycopene is produced at days 5-6 of culture.

27. Process according to claim 26, wherein at least 30 mg of lycopene is produced per gram of dry weight of mycelium at days 5-6 of culture.

28. Process according to claim 13, wherein step b. is carried out by previously separating the biomass from the culture medium and resuspending said biomass in alcohol, with an alcohol/biomass ratio of the order of 1 ml/g to 10 ml/g.

29. Process according to claim 13, wherein in step b., alcohol is used at a temperature between 0° C. and that corresponding to its boiling point, preferably between 10° and 50° C.

30. Process according to claim 13, wherein step b. is carried out directly by mixing the fermentation culture medium containing the biomass without separating previously said biomass, in alcohol, with a culture medium/alcohol ratio between 1/0.5 and 1/5, at a temperature between room temperature and the boiling point of the mixture.

31. Process according to claim 13, wherein a solvent selected from the group consisting of ethyl acetate, propyl acetate, isopropyl acetate, n-butyl acetate and isobutyl acetate, is used in step d. of solid-liquid extraction.

32. Process according to claim 31, wherein a quantity of solvent of the order of 5 to 30 ml is used per g of the biomass resulting in step c.

33. Process according to claim 31, wherein the solvent is isobutyl acetate and the extraction is carried out at temperatures ranging between 60-70±5° C.

34. Process according to claim 33, wherein the solvent is used in such a way that the time of contact with the lycopene is less than 15 minutes.

35. Process according to claim 13, wherein in step f., precipitation/crystallization of the concentrated product after extraction is effected by adding a solvent in which the lycopene has low solubility, and which ensures that the substances of a lipophilic character accompanying the lycopene remain dissolved.

36. Process according to claim 13, comprising a formulation step h. comprising formation of a microcrystalline suspension of lycopene by premixing the lycopene crystals, antioxidants and oils followed by milling.

37. Process according to claim 36, in which the oil is of vegetable origin.

38. Process according to claim 36, wherein milling is carried out in a ball mill.

39. Process according to claim 36, wherein liposoluble antioxidants are used in a proportion from 0.2 to 15% relative to the weight of the lycopene in the mixture.

40. Process according to claim 13, comprising a formulation step h. comprising the preparation of cold-water-dispersible (CWD) lycopene with the following steps:
i) Dissolution of the crystalline lycopene accompanied by antioxidant compounds in an organic solvent;

ii) Emulsion and/or microencapsulation of the aforesaid organic phase in an aqueous solution of modified starches;

iii) Elimination of the solvent and some of the water by evaporation, obtaining the liquid formulation; and iv) Drying and finishing.

41. Process according to claim 40, wherein methylene chloride is used as solvent in step i. of dissolution of the lycopene.

42. Process according to claim 40, wherein an acyl esters is used as solvent in step i. of dissolution of the lycopene.

43. Process according to claim 40, wherein one or a mixture of antioxidants is used in step i. of dissolution of the lycopene, in a proportion between 1-30%, relative to the weight of the lycopene.

44. Process according to claim 40, wherein in addition a vegetable oil is used in step i. for dissolution of the lycopene in the organic solvent.

45. Process according to claim 40, wherein a modified starch is used as emulsifying and/or microencapsulating agents in step ii.

46. Process according to claim 40, wherein in step iv. the drying of the liquid formulation is effected by a process selected from the group consisting of: atomization by high-temperature pulverization, granulation by pulverization on a fluidized bed at relatively low temperature and freeze-drying.

47. Process according to claim 46, wherein the drying by granulation performed in step iv. is carried out by atomisation and the atomized product obtained is agglomerated in a fluidised bed process by pulverization of a solution of one of the modified starches or the suspension of microencapsulated lycopene, thus obtaining a granulated product of increased particle size.

48. Process according to claim 46, in which the granulation comprises spraying a microencapsulated lycopene suspension over a seed material.

49. Process according to claim 40, wherein in step iv, the finishing comprises coating the particles with aqueous solutions of sugars or modified starches in a proportion of 0.5-10%.

50. Crystalline lycopene having a crystal purity, determined by spectrophotometric absorption of the crystals in n-hexane at 472 nm (E1% 1 cm=3450), greater than 95%, said crystalline lycopene being obtainable by a process comprising the following steps in succession a. mixing (+) and (−) lycopene overproducer strains of *Blakeslea trispora*, whose ages of vegetative stage of growth has been controlled, in a culture medium biomass in suitable fermentation conditions for producing lycopene;

b. treatment of the culture medium biomass of step a) with alcohol and separation of a wet, purified biomass;

c. conditioning of the wet, purified biomass by drying and disintegration or breaking;

d. solid-liquid extraction of the lycopene contained in the purified biomass with an organic solvent, controlling the temperature and the time of dissolution in function of the organic solvent used;

e. concentration of the enriched lycopene extract;

f. precipitation/crystallization of the lycopene from the concentrated extract by addition of alcohol to form a crystalline liquor; and g. filtration of crystals of lycopene from the crystalline liquor and drying to obtain the crystalline lycopene such that, when the crystalline lycopene is subjected to high pressure liquid chromatography, no carotenoid other than lycopene is detected.

51. The crystalline lycopene according to claim 50, wherein, when the crystalline lycopene is subjected to high pressure liquid chromatography, neither a carotenoid other than lycopene nor cis lycopene is detected.

* * * * *